US008100827B2

(12) United States Patent
Farley

(10) Patent No.: US 8,100,827 B2
(45) Date of Patent: Jan. 24, 2012

(54) ADJUSTABLE RAIL CLAMP

(75) Inventor: Daniel Farley, Traverse City, MI (US)

(73) Assignee: Thompson Surgical Instruments, Inc., Traverse City, MI (US)

( * ) Notice: Subject to any disclaimer, the term of this patent is extended or adjusted under 35 U.S.C. 154(b) by 266 days.

(21) Appl. No.: 12/466,489

(22) Filed: May 15, 2009

(65) Prior Publication Data

US 2009/0287062 A1    Nov. 19, 2009

Related U.S. Application Data

(60) Provisional application No. 61/053,472, filed on May 15, 2008.

(51) Int. Cl.
*A61B 1/32* (2006.01)
*F16B 7/10* (2006.01)
(52) U.S. Cl. ............ 600/230; 403/109.3; 403/322.2
(58) Field of Classification Search ............ 600/231, 600/230; 403/322.2, 325, 23, 36, 185, 109.3
See application file for complete search history.

(56) References Cited

U.S. PATENT DOCUMENTS

| | | | | |
|---|---|---|---|---|
| 1,505,422 | A | * | 8/1924 | Potter ................ 403/26 |
| 1,747,799 | A | | 9/1928 | Straus |
| 3,970,075 | A | * | 7/1976 | Sindelar et al. ........... 600/231 |
| 4,099,521 | A | | 7/1978 | Nestor et al. |
| 4,254,763 | A | | 3/1981 | McCready et al. |
| 4,355,631 | A | | 10/1982 | LeVahn |
| 4,938,622 | A | * | 7/1990 | Stoerzbach .............. 403/2 |
| 4,971,038 | A | | 11/1990 | Farley |
| 5,025,780 | A | | 6/1991 | Farley |
| 5,109,831 | A | * | 5/1992 | Forrest et al. ............... 600/228 |
| 5,372,147 | A | | 12/1994 | Lathrop, Jr. et al. |
| 5,400,772 | A | | 3/1995 | LeVahn et al. |

(Continued)

FOREIGN PATENT DOCUMENTS

IT              446439          6/1950

(Continued)

OTHER PUBLICATIONS

Marshall, Samuel F. et al. "New, table-supported, self-retaining retractor," Surgery, pp. 477-479. Sep. 1963.

*Primary Examiner* — Eduardo C Robert
*Assistant Examiner* — Jacqueline Johanas
(74) *Attorney, Agent, or Firm* — McAndrews, Held & Malloy, Ltd.

(57) ABSTRACT

An adjustable surgical retractor system for clamping system to an operating table. The clamping mechanism includes an upper jaw, lower jaw, a drive member, an adjustable frame support post and releasable locking mechanism for adjusting the height of the surgical retracting frame. The releasable locking mechanism can be a mechanism that includes a sleeve in close sliding relationship to the upper portion of lower jaw member. The upper portion of the lower jaw has a plurality of sockets for receipt of a plurality of balls. The sleeve can have a first position which positions an internal shoulder in alignment with the sockets and urges the balls into engagement with circumferential grooves in post member to lock the post at desired height. In a second position, an internal groove in the sleeve can align with the sockets to allow the balls to move partially out of the sockets and out of engagement with the groove in the post so that the post can be longitudinally adjusted relative to the clamping mechanism.

8 Claims, 11 Drawing Sheets

U.S. PATENT DOCUMENTS

| | | | |
|---|---|---|---|
| 5,555,897 | A | 9/1996 | Lathrop, Jr. et al. |
| 5,597,146 | A | 1/1997 | Putman |
| 5,603,689 | A | 2/1997 | Lucini |
| 5,704,900 | A | 1/1998 | Dobrovolny et al. |
| 5,741,210 | A | 4/1998 | Dobrovolny |
| 5,813,296 | A * | 9/1998 | Hoff et al. ............... 81/177.85 |
| 5,908,382 | A | 6/1999 | Koros et al. |
| 6,017,008 | A | 1/2000 | Farley |
| 6,042,541 | A | 3/2000 | Dobrovolny et al. |
| 6,315,718 | B1 | 11/2001 | Sharratt |
| 6,511,423 | B2 | 1/2003 | Farley |
| 6,530,883 | B2 | 3/2003 | Bookwalter et al. |
| 6,663,563 | B1 | 12/2003 | Sharratt |
| 6,792,830 | B2 | 9/2004 | DeKeuster et al. |
| 6,808,493 | B1 | 10/2004 | Bookwalter et al. |
| 7,013,765 | B2 * | 3/2006 | Chang ...................... 81/177.2 |
| 7,232,411 | B2 * | 6/2007 | Dinkler et al. ............ 600/233 |
| 2002/0026101 | A1 | 2/2002 | Bookwalter et al. |
| 2002/0177753 | A1 | 11/2002 | Dobrovolny |
| 2005/0113645 | A1 | 5/2005 | Sharratt et al. |
| 2006/0052673 | A1 | 3/2006 | Santilli |
| 2006/0063977 | A1 | 3/2006 | Sharratt et al. |
| 2006/0253109 | A1 | 11/2006 | Chu |

FOREIGN PATENT DOCUMENTS

| | | |
|---|---|---|
| SU | 1210800 | 2/1986 |

\* cited by examiner

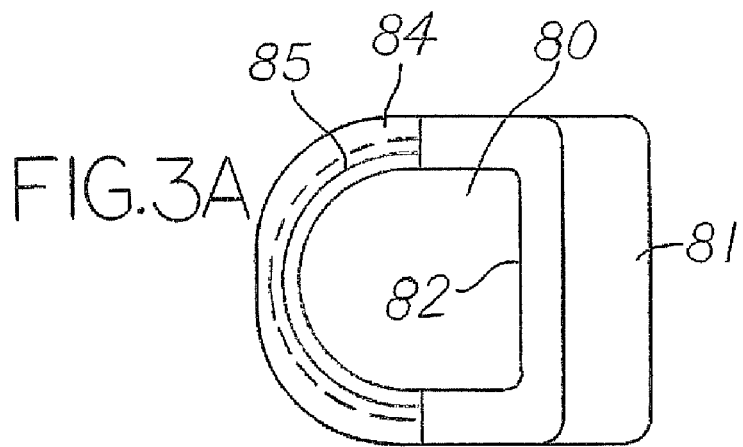
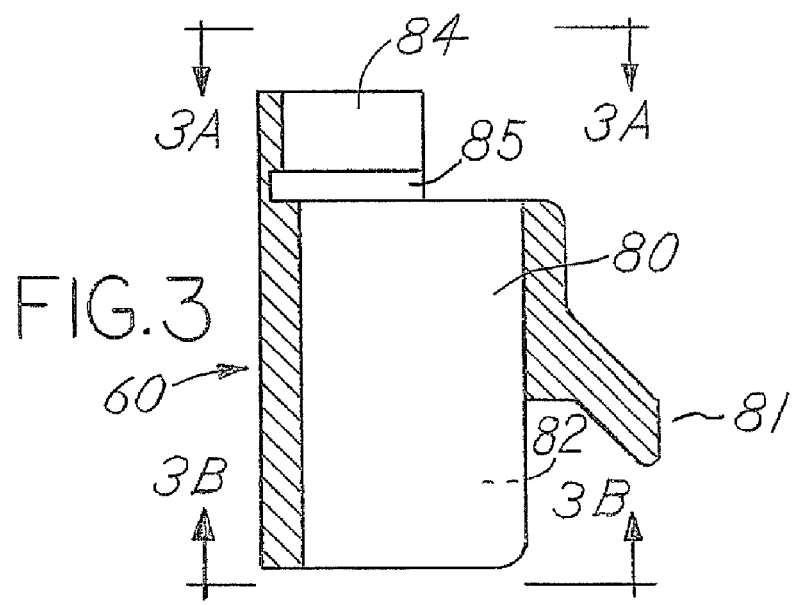
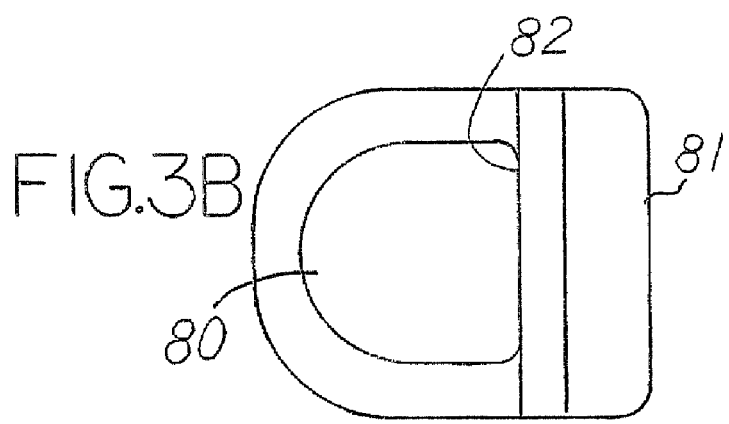

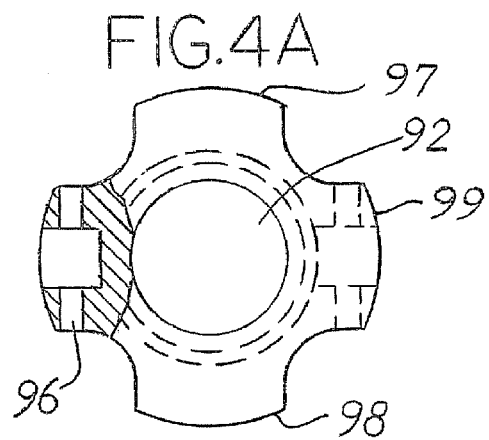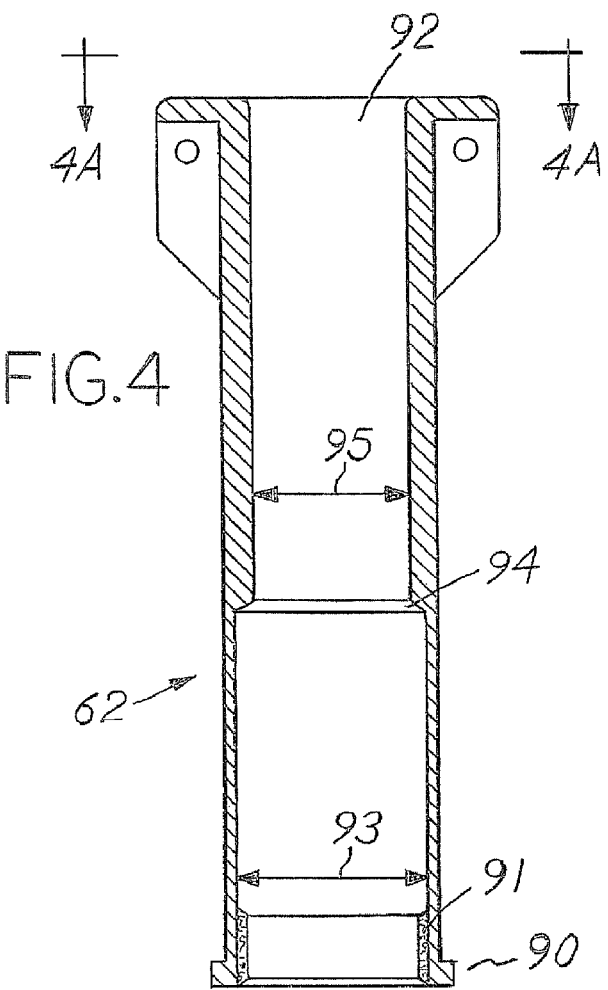

FIG.5A
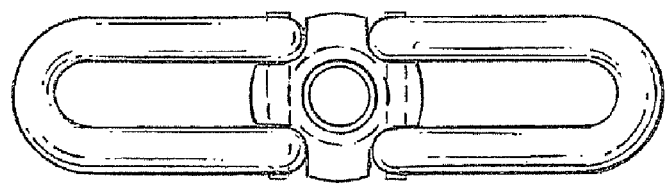
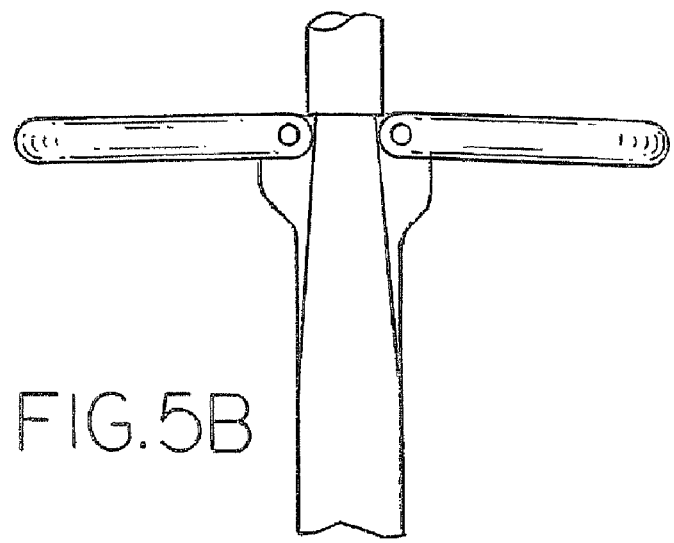
FIG.5B
FIG.5C

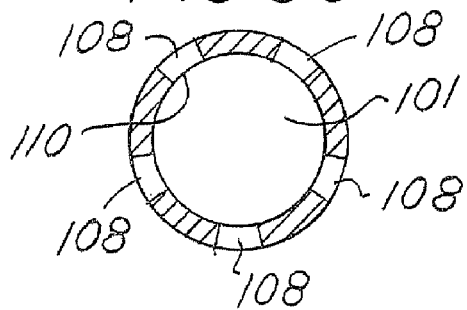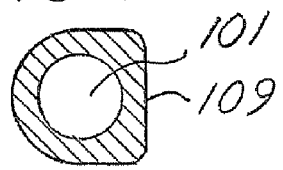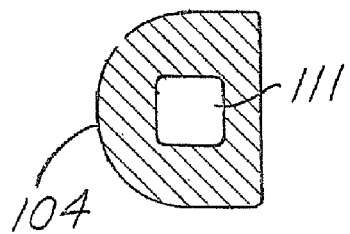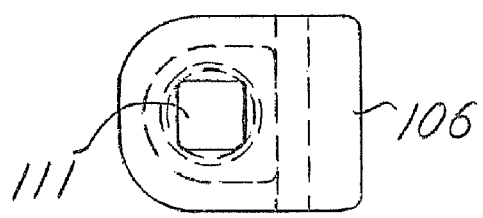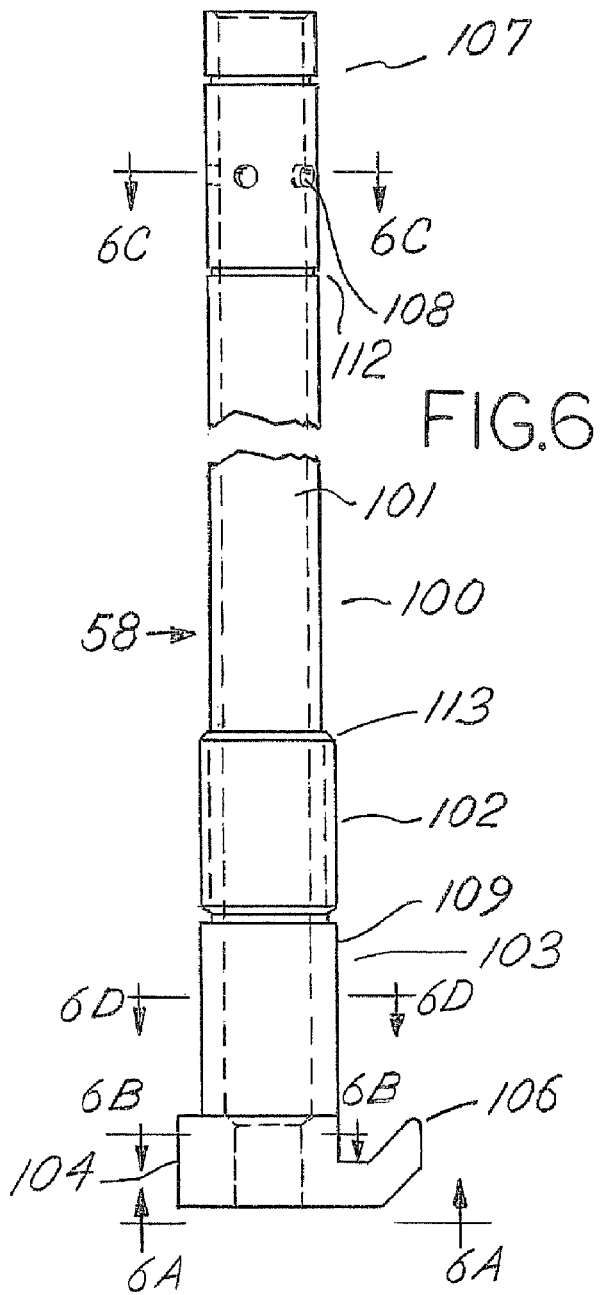

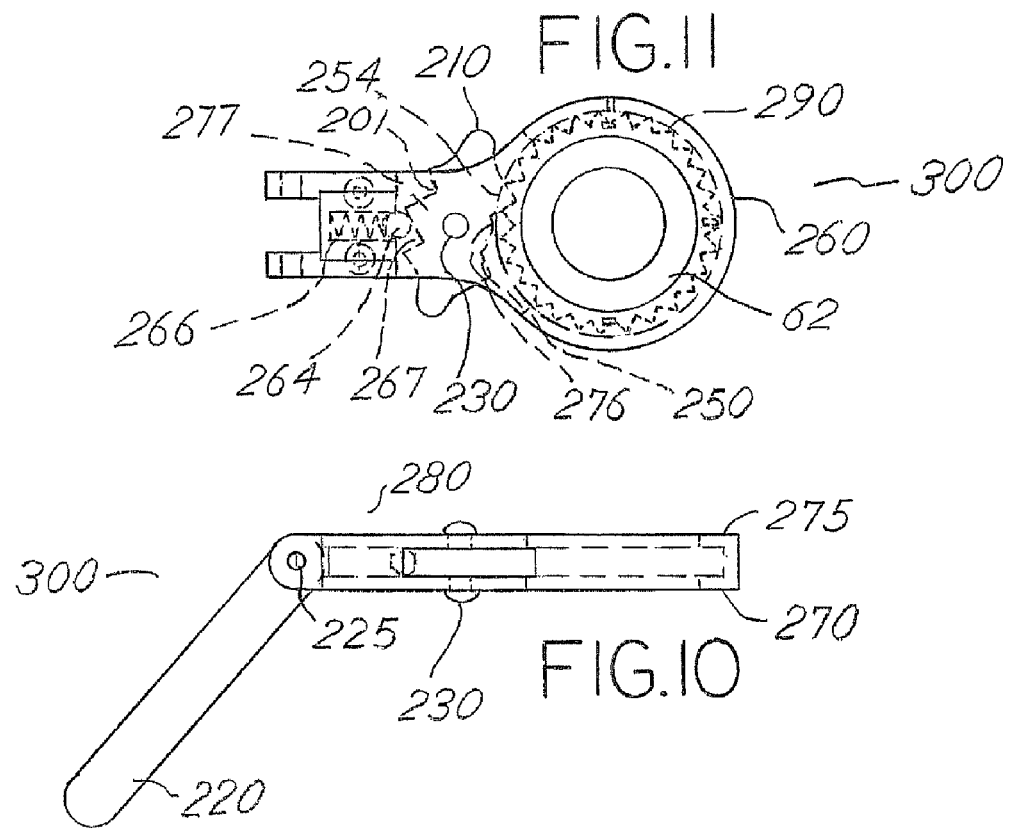
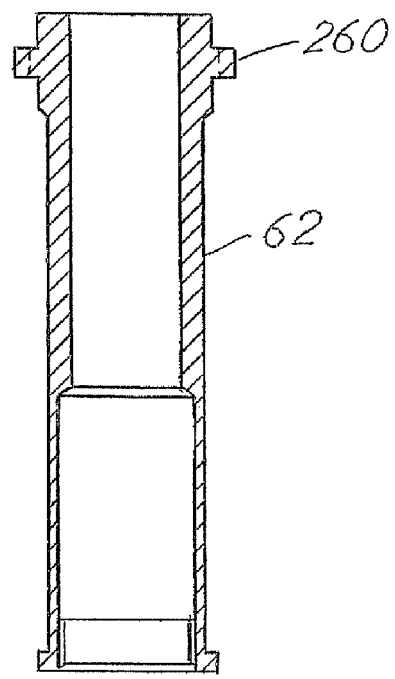

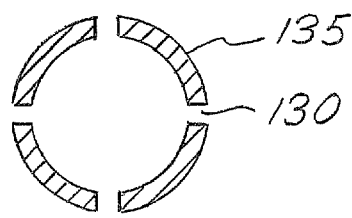
FIG.12C
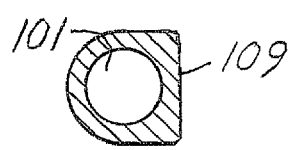
FIG.12D
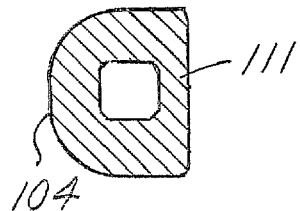
FIG.12B
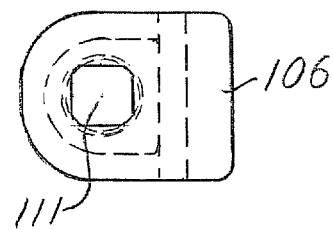
FIG.12A
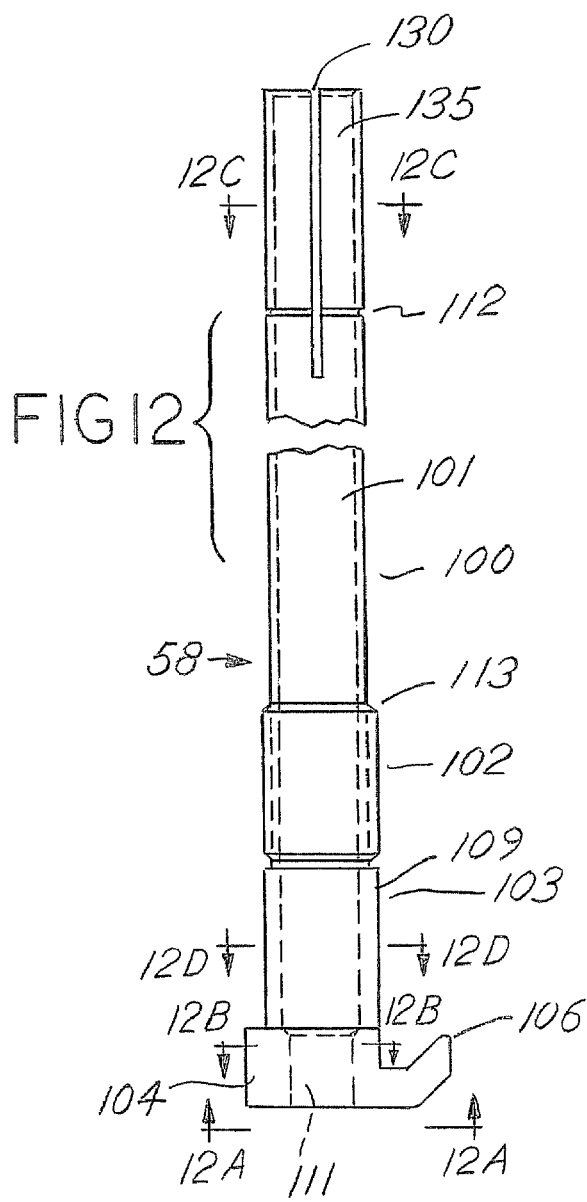

ial position of the surgical retractor to the post into a non-clamping position. With the clamp in a non-clamping position, the vertical position of the surgical retractor can then be repositioned into a new position. The surgical retractor is then secured to the post be placing the clamp in the clamping position. This procedure may add additional time to the surgical procedure, require additional personnel to perform the vertical adjustment and cause unneeded inconvenience to the surgical personnel.

ADJUSTABLE RAIL CLAMP

RELATED APPLICATIONS

This application makes reference to, claims priority to and claims benefit from U.S. Provisional Patent Application Ser. No. 61/053,472, entitled "Adjustable Rail Clamp" and filed on May 15, 2008.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention relates to surgical apparatus for retracting anatomy to provide exposure of the operative site, and more particularly relates to a retraction apparatus that is sturdy, adjustable, and conducive to thorough sterilization.

During surgical procedures, a surgeon will typically make an incision in a patient to access the sites of interest, such as internal organs and bone structures, for a particular procedure. A surgical retractor system is typically utilized to maintain clear access to the site of interest. Retractors are designed to hold back the anatomy in the immediate area of the operative site to enable a surgeon to have both an optimal view of the site and a sufficiently open area within which to work.

The usefulness of any retractor device is necessarily limited by the number of ways that the retractor can be positioned with respect to the retracted anatomy as well as the ease with which the surgeon can adjust the relative position of the retractor both before and during surgery. The less obstructive and more versatile a retractor device is, the more desirable it becomes for use in the above-described manner. Thus, variance in types of surgery and patient size necessitates surgical retractor systems that are adjustable. In addition, equipment sterilization requirements call for a device that can be thoroughly cleansed by conventional means in a safe and easy manner.

A surgical retractor system typically consists of a rail clamp, a frame connected to the rail clamp, and retractor blades that are clamped to the frame. The rail clamp is commonly secured to an operating table and provides a fixed and sturdy support for the frame and the retractor blades. Each of the components in a typical surgical retractor system is conventionally made of stainless steel, although, as disclosed in U.S. Pat. No. 6,033,363, parts of the system may be made from a nonconductive material. The reason that stainless steel is generally used is that stainless steel is easily sterilized. As would be expected, before any use of the surgical retractor system can be made during a surgical procedure, the system must be thoroughly sterilized for the protection of the patient. This sterilization is performed in the standard methods well known in the art.

Often, a surgical retractor system frame includes one or more posts, each connected to the operating table by a rail clamp. Typically, some form of support structure for supporting retractor blades is connected to the post(s) by clamps. During surgical procedures, it is preferable that the surgical retractor system frame be adjustable to quickly position the retractor in a precise position. Prior art support structures generally repositioned the height of the surgical retractor by positioning the clamp connecting the surgical retractor to the post into a non-clamping position. With the clamp in a non-clamping position, the vertical position of the surgical retractor can then be repositioned into a new position. The surgical retractor is then secured to the post be placing the clamp in the clamping position. This procedure may add additional time to the surgical procedure, require additional personnel to perform the vertical adjustment and cause unneeded inconvenience to the surgical personnel.

BRIEF SUMMARY OF THE INVENTION

The system includes an adjustable clamp for clamping the system to an operating table, a post supporting member, and a frame which includes extension arms and retractor blades. A releasable locking mechanism is provided to releasably adjust the height of the retractor frame for quick and easy adjustment.

In accordance with one aspect of the technology, the system comprises a clamping mechanism including a lower jaw, upper jaw and a jaw drive member to adjust the upper and lower jaws to fasten the system to a surgical operating table. A post frame member is located in the inner space of the lower jaw member. In addition, the device includes a locking device to releasably adjust the position of the post frame support member in relation to the clamping mechanism. The locking device is comprised of an outer sleeve slidably placed over the upper portion of the lower jaw member. Located in between the sleeve and the lower jaw member are a plurality of curved surface members. The sleeve has an internal circumferential shoulder to urge the curved surface members into sockets in lower jaw and grooved spaces that allow the curved members to partially retract from engagement of the sockets in the lower jaw. The sockets in the lower jaw are of such a dimension that part of the curved surface members is allowed to partially protrude into the lower jaw inner space. The post frame member has spaced circumferential grooves which are engaged and disengaged by the partially protruding curved surface members as the sleeve is positioned to engage or disengage the curved surface members.

Another aspect of the technology provides a reversible ratchet assembly engaged on the jaw drive member through a plurality of ratchet gear teeth on the jaw drive member. The ratchet assembly comprises a handle with a ratchet head on the handle; the ratchet head includes a pivotal pawl, a compression spring, and a ball. The pivotal pawl is movable between a first position and a second position. Movement of the pivotal pawl to the first position causes the pawl to engage the ratchet gear teeth on the jaw drive member allowing for a ratcheting rotation of the jaw drive member in a first direction. Movement of the pivotal pawl to the second position causes the pawl to engage the ratchet gear teeth on the jaw drive member allowing for a ratcheting rotation of the jaw drive member in a second direction.

A further embodiment of the present technology provides for an alternative locking device to releasably adjust the position of the post frame support member in relation to the clamping mechanism. The alternative locking device comprises a clamp apparatus that is operatively attached to the upper portion of the lower jaw member which contains a plurality of slots. The clamping apparatus includes a clamp and a cam member that is attached to the clamp through a shaft member. The operation of the cam member urges the clamp between an unclamped position and a clamped position. In the clamped position, the clamp closes around the slotted portion of the lower jaw member and compresses the upper portion of the lower jaw member to engage the adjustable post frame support member and prevent the movement of the adjustable post frame support member. In the unclamped position, the absence of compression of the slotted portion allows the slotted portion of the lower jaw member to return to its original position thus allowing the unlocking of the post frame support member.

BRIEF DESCRIPTION OF SEVERAL VIEWS OF THE DRAWINGS

FIG. 3 is an illustration of an upper jaw member of the rail clamp illustrated in FIG. 2.

FIGS. 3A and 3B are top and bottom views of the upper jaw member.

FIG. 4 is a cross sectional view of a jaw drive member of the rail clamp illustrated in FIG. 2.

FIG. 4A is a top view of the jaw drive member.

FIGS. 5A, 5B, and 5C are top and side views of the handle portion of jaw drive member of FIG. 4.

FIG. 6 is a side view of the lower jaw member of the rail clamp of FIG. 2.

FIG. 9 is a cross sectional view of a jaw drive member of the rail with ratchet teeth.

FIG. 10 is a cross sectional side view of the ratchet assembly.

FIG. 11 is a cut away top view of the ratchet assembly cooperatively engaged on the ratchet teeth of the jaw drive member.

FIG. 12 is a side view of the lower jaw member of the rail clamp with slotted upper portion.

DETAILED DESCRIPTION OF THE INVENTION

Figure 1:
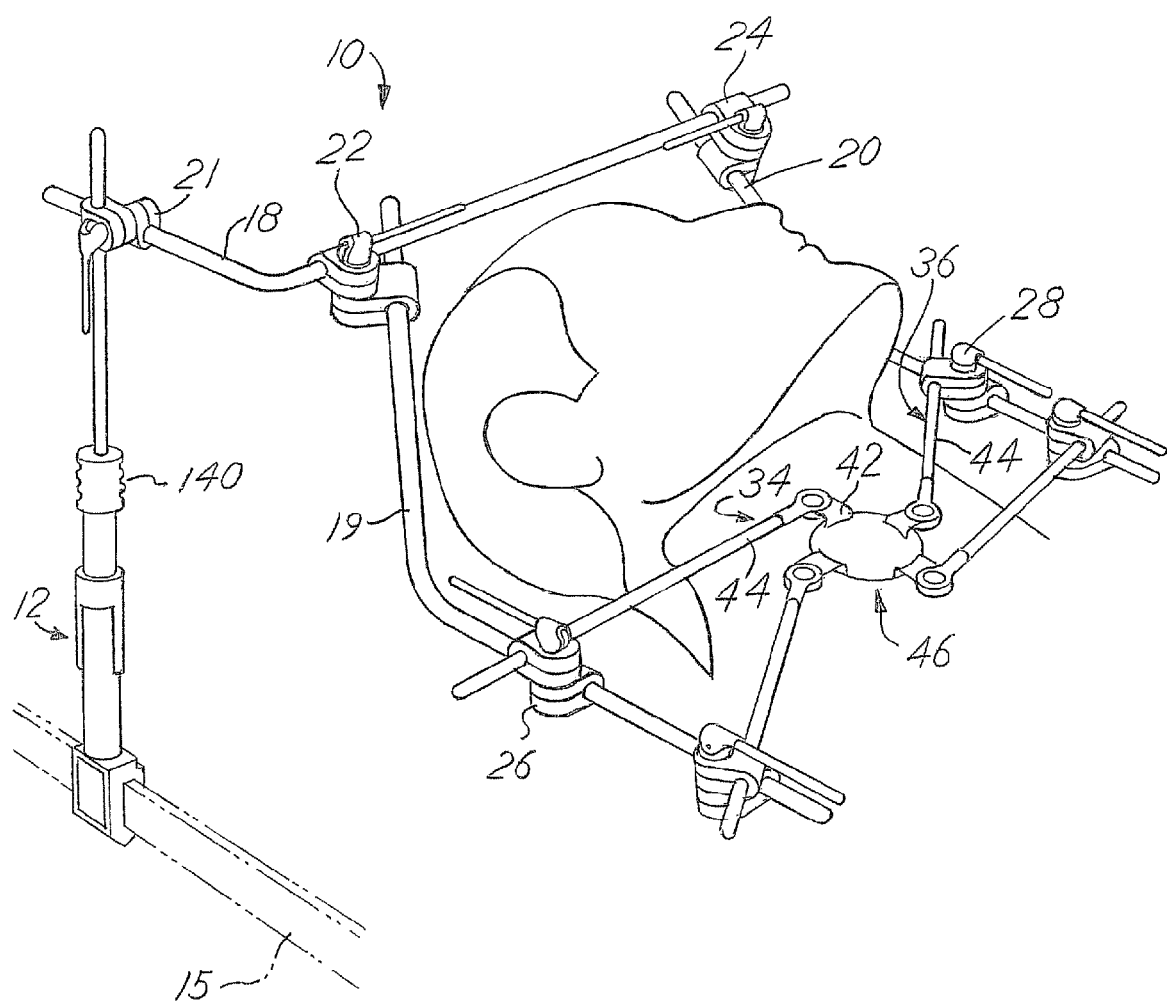
FIG. 1 is a perspective view of a surgical retractor system.

As shown in FIG. 1, a surgical retraction system 10 includes an adjustable rail clamp 12 which is securable to a horizontal rail 15 of a conventional operating table (not shown). An adjustable post 17 extends vertically from the adjustable rail clamp assembly 12 to provide support for a cross bar 18 which in turn provides support for a pair of extension arms 19, 20. The cross bar 18 is secured to the adjustable the adjustable post 17 by a universal joint clamp 21. Extension arms 19, 20 are respectively secured to the cross bar 18 by a pair of universal joint clamps 22, 24. Additional joint clamps 26, 28 may be disposed along the extension arms 19, 20 for rigidly securing any number of retractor blades 34, 36 to the extension arms 19, 20. As will suggest itself, the extension arm 19 can also be secured directly to the adjustable the adjustable post 17 by a universal joint clamp. The adjustable post 17 may be adjusted vertically through a slide locking mechanism 140.

Each retractor blade 34, 36 may include a blade portion 42 and a retractor arm 44. The blade portion 42 preferably extends downwardly into an incision 46 made by a surgeon. The blade portion 42 may be used to retract anatomy to make the incision 46 accessible to the surgeon.

Figure 2:
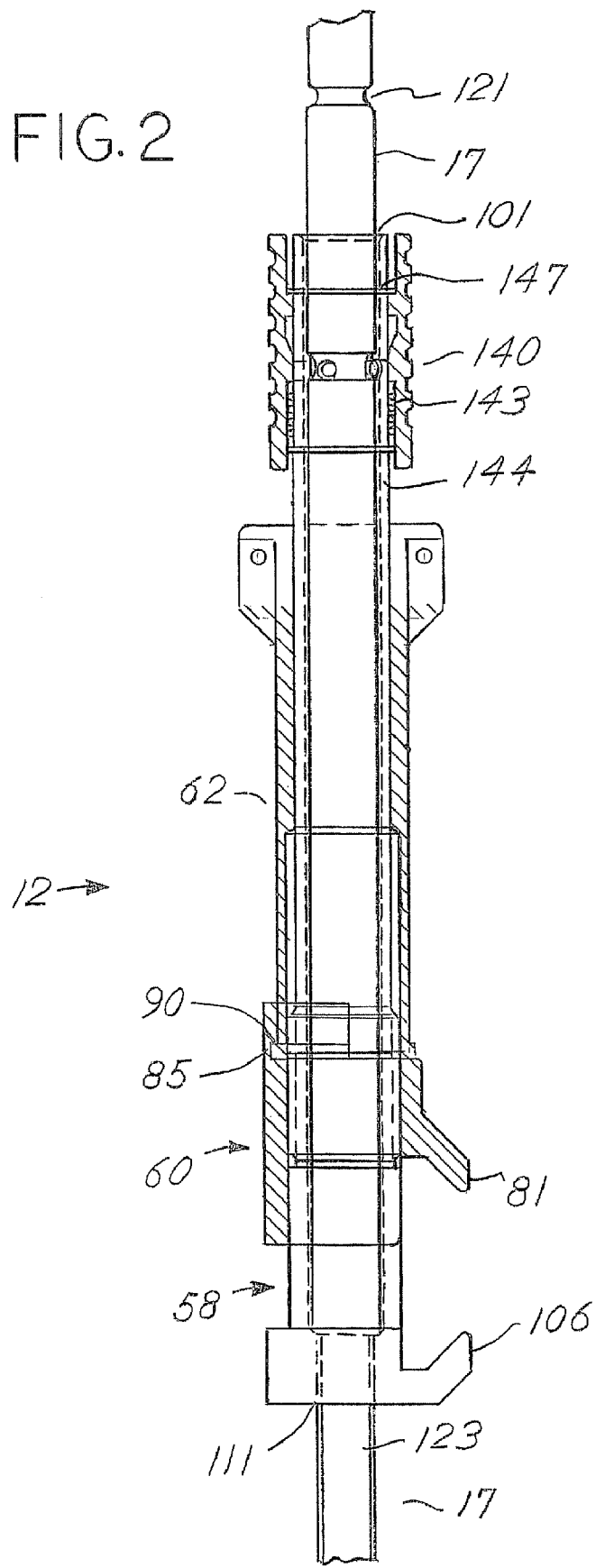
FIG. 2 is an elevated view of a rail clamp assembly with a quick release slide lock for quick height adjustment of support post.

As is shown in FIG. 2, the adjustable rail clamp assembly 12 preferably is formed from a lower jaw member 58, an upper jaw member 60, and a jaw drive member 62. The adjustable rail clamp assembly components 58, 60, 62 are associated with the adjustable post 17 such that the adjustable post 17 may be slidably inserted into lower the internal space 101 of lower jaw member 58. The slide locking mechanism 140 may be slidably secured to the upper portion 100 of the lower jaw member 58 by snap rings 144, 147.

As can be seen in FIG. 2, the upper jaw member 60 can be positioned over the lower jaw member 58. The jaw drive member 62 can then be rotatably mounted to the upper jaw member 60. The adjustable post 17 can then be inserted into a space 101 of the jaw drive member 62. The adjustable post 17 extends thru the entire adjustable rail clamp assembly 12 and a lower portion 123 of the adjustable post 17 exits out a non-cylindrical bore hole 111 of the lower jaw member 58. As will be explained in detail later, the clockwise rotation of the jaw drive member 62 drives the upper jaw member 60 downward forcing the upper jaw member 60 and the lower jaw member 58 toward one another to engage the table rail 15.

Referring to FIGS. 2, 3, 3A, 3B, the upper jaw member 60 preferably has an outside surface that is generally D shaped. Other shapes are also contemplated. Further, the upper jaw member 60 may have a generally D shaped hollow area 80 disposed along its longitudinal axis. The upper end of the upper jaw member 60 preferably includes a semicircular bored section 84 having a guide slot 85. Also, the upper jaw member 60 preferably has a upper lip 81 that protrudes outwardly and downwardly from the upper jaw 60 for engaging the table rail 15. The upper jaw member 60 is preferably positioned over the lower jaw member 58. A flat portion 82 of the generally D-shaped hollow area 80 is sized to co-operate with a flat portion 109 of the lower jaw member 58 shown in FIG. 6D.

Referring to FIGS. 2, 3 and 4, the jaw drive member 62 is preferably rotatably mounted to the upper jaw member 60 by an annular flange 90 formed at the lower end of the jaw drive member 62. The guide slot 85 in the upper end of the upper jaw member 60 is sized to receive the annular flange 90 of the jaw drive member 62. During assembly, the annular flange 90 of the jaw drive member 62 is laterally moved into the guide slot 85 of the upper end of the upper jaw member 60. This cooperation prevents vertical separation of the upper jaw carrying member 60 from the jaw drive member 62 while permitting rotation of the jaw drive member 62 relative to the upper jaw member 60. As the upper jaw member 60 is driven downwardly to engage the top of table rail 15, the flat portion 82 of the opening 80 in the upper jaw member 60 slides over the flat side 109 of the lower portion 103 of the lower jaw member 58. This prevents rotational movement of the upper jaw member 60 as the jaw drive member 62 is rotated.

As shown in FIG. 4, the jaw drive member 62 includes a set of internal thread set 91 formed within a cylindrical bore 92. A diameter 93 of the thread set 91 is larger than a diameter 95 of the upper portion of the cylindrical bore 92 above the thread set 91. Also, as shown in FIG. 4A, the top of the jaw drive member 62 is formed with four protruding areas 96, 97, 98, 99.

Referring to FIGS. 5A, 5B, and 5C, a pair of manual control handles 86, 87 are disposed at the uppermost end of the jaw drive member 62. The control handles 86, 87 may be generally U-shaped and preferably pivotally fastened to the jaw drive member 62 by pins 88, 89. As shown in FIG. 5A, the top of the jaw drive member 62 is formed with the four protruding areas 96, 97, 98, 99. The protruding area 96, 99 may serve as bearings for the pins 88, 89. The control handles 86, 87 permit operation of the rail clamp via rotation of the control handles 86, 87.

Referring to FIGS. 6, 6A, 6B, 6C, and 6D, an upper exterior portion 100 of the lower jaw member 58 is preferably generally circular in shape with a cylindrical bore 101 for receiving a circular portion 120 (FIG. 7) of the adjustable post 17. An exterior lower portion 102 of the cylindrical portion 100 of the lower jaw member 58 is threaded. Referring to FIG. 6B and FIG. 6D, after the threaded portion 102 of the lower jaw member 58, an exterior shape 103 of the lower jaw member 58 may transition from the circular shape 100 into a general D shape 109. The cylindrical bore 101 may continue through D shaped portion 103 for receiving the circular portion 120 of the adjustable post 17. Referring to FIGS. 6 and 6B, a lower portion 104 of the lower jaw member 58 is preferably D shaped. The lower portion 104 of the lower jaw member 58 has a rectangular bore 111 for receiving a rectangular portion 123 of the adjustable post 17. A lower lip 106 protrudes outwardly and upwardly from the lower jaw member 58 for engaging the table rail 15.

The exterior upper portion 100 of the lower jaw member 58 has two spaced apart slots 107, 112. In between the spaced apart slots 107, 112, the lower jaw member 58 has a plurality of frustum-conical holes 108 for receiving a curved surface member 142 shown on FIG. 8.

As shown in FIG. 6, the lower jaw member 58 has a reciprocal set of threads 102 which surround the lower portion of the lower jaw member 58. Referring to FIGS. 2, 4, and 6, the threads 91 in the jaw drive member 62 and the threads 102 of the lower jaw member 58 preferably engage each other as the jaw drive member 62 is manually rotated in a clockwise direction. Rotation of the jaw drive member 62 drives the upper jaw member 60 downwardly, forcing the lower lip 106 of the lower jaw member 58 and the upper lip 81 of the upper jaw member 60 toward one another to engage the table rail 15. The jaw drive member 62 is rotated until the lower jaw lip 106 on lower jaw member 58 and the upper jaw lip 81 of the upper jaw member 60 securely tighten against the rail 15.

The counter clockwise rotation of the jaw drive member 62 causes the upper jaw member 60 to recede from the lower jaw member 58. Continued counter clockwise rotation of the jaw drive member 62 may cause complete separation of the thread sets 91, 102. With the upper jaw member 60 disengaged from the lower jaw member 58, the thread sets 91, 102 become exposed for cleaning. The reduction in diameter at a location 94 of the jaw drive member 62 shown in FIG. 4 contacts an angled periphery surface 113 of the lower jaw member 58 to control the extent of opposing movement of the lower jaw member 58 and the upper jaw member 60.

Figure 7:
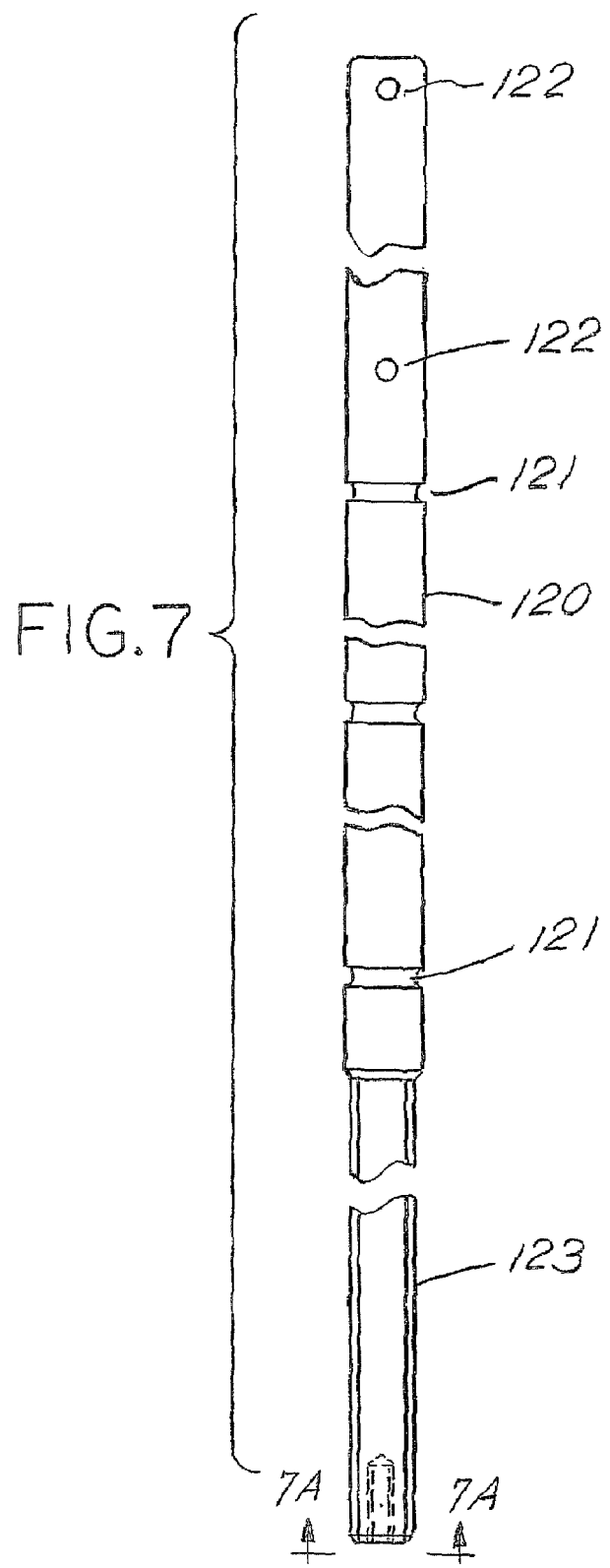
FIG. 7 is a side view of one embodiment of a vertical support post.
Figure 7A:

FIG. 7 illustrates at least one aspect of the adjustable post 17. As shown in FIG. 7, the upper portion 120 of the adjustable post 17 is preferably generally cylindrical. The upper portion 120 of the adjustable post 17 includes at least a groove 121. Those skilled in the art will realize that more than one groove 121 is preferable. Further, the upper portion 120 of the adjustable post 17 may include a plurality of pin holes 122 for receiving pins to position universal clamps 21 on the end of the adjustable post 17.

The lower portion 123 of the adjustable post 17 is preferably non-cylindrical. Referring to FIG. 2 and FIG. 6, the adjustable post 17 is inserted into the bored out section 101 of the lower jaw member 58 with the non-cylindrical end 123 inserted first until the non-cylindrical end engages the non-cylindrical bored hole 111 in the lower jaw member 58. The engagement of the non-cylindrical lower section 123 of the adjustable post 17 with the non-cylindrical bore hole 111 of the lower jaw member 58 prevents the adjustable post 17 from rotating.

Referring again to FIGS. 2, 3 and 4, the adjustable the adjustable post 17 extends upwardly through a hollow area 80 in the upper jaw member 60 and the cylindrical bore 92 formed in the jaw drive member 62.

Figure 8:
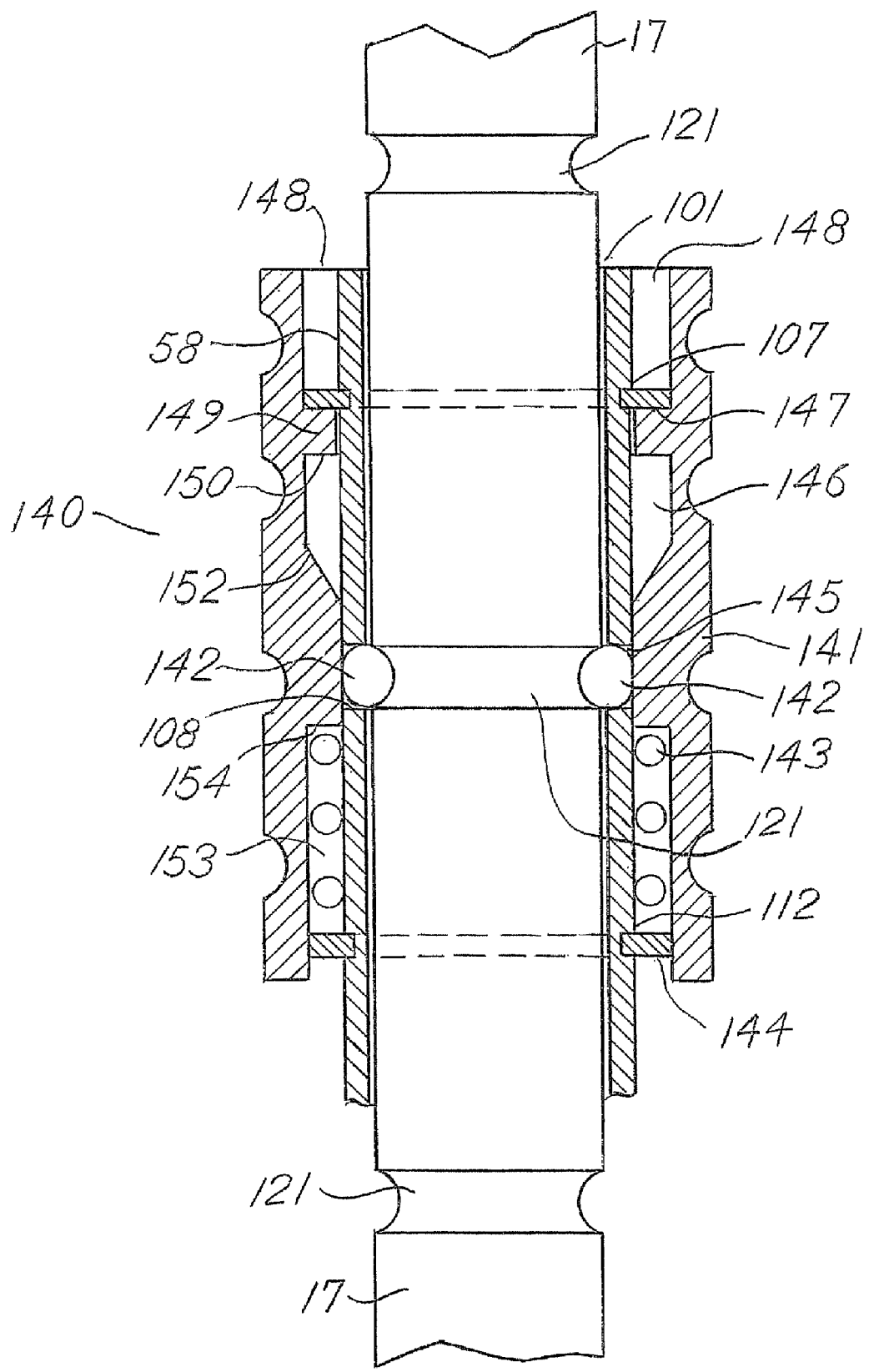
FIG. 8 is a cross section view of one aspect of the slide lock assembly.

FIG. 8 is a cross sectional view of one aspect of the slide locking mechanism 140. The slide locking mechanism 140 preferably includes a slide lock sleeve 141, a spring 143, snap rings 144, 147 and a plurality of curved surface members 142 such as ball bearings. The slide locking mechanism 140 permits a quick adjustment of the retractor assembly height through the longitudinal adjustment of the adjustable post 17. Slide lock sleeve 141 is bored to have a minimum opening to allow the slide lock sleeve 141 to be slidably inserted over the upper portion 100 of the lower jaw member 58. To retain the slide lock sleeve 141 of the slide locking mechanism 140 on the upper portion 100 of the lower jaw member 58, snap rings 144, 147 may be inserted into the slot 107 and the slot 112 of the lower jaw member 58. The slots 107 and 112 are spatially located on the upper portion 100 of the lower jaw member 58. The snap ring 147 preferably limits upward longitudinal movement of slide lock sleeve 141. The snap ring 144 preferably limits the downward longitudinal movement of slide lock sleeve 141.

The slide lock sleeve 141 preferably has a bore comprised of several inner diameters. The slide lock sleeve 141 has a first axial bore 148. After the bore 148, preferably a second reduced dimension bore 149 may be made in the slide lock 141 forming an internal shoulder 150. The internal shoulder 150 is of such a dimension that it engages the snap ring 147, thereby limiting upward longitudinal movement of the slide lock sleeve 141. Preferably after the second bore 149 forms the shoulder 150, a third bore channel 146 may be formed in the slide lock sleeve 141 preferably having a greater diameter bore than bore 149. The channel 146 has an angular transition 152 to a fourth axial bore 145. The axial bore 145 preferably has a bore diameter greater than groove 146 diameter and the bore diameter of the channel 146 is slightly greater than the outside diameter of the upper portion 100 of the lower jaw member 58 allowing the slide lock sleeve 141 to slidably move over the upper portion 100 of the lower jaw member 58. After the bore 145, the slide lock sleeve 141 may have a fifth axial bore 153. The diameter of the axial bore 153 is preferably greater than the diameter of the bore 145 thus creating a shoulder 154. Bore 153 is capable of receiving a spring 143. The spring 143 is bounded by the shoulder 154 on the upper end and the snap ring 144 on the lower end.

As shown in FIG. 8, a plurality of curved surface members 142, for example ball bearings, are inserted in the frustum-conical holes 108 in the lower jaw member 58. As shown in FIG. 6C, the frustum-conical holes 108 preferably are provided with an end diameter 110 that is smaller than the diameter of the curved surface members 142, but large enough to permit a portion of the curved surface members 142 to extend into the opening 101 of the lower jaw member 58.

As shown in FIG. 2 and FIG. 8, the adjustable post 17 is inserted into the space 101 of the lower jaw member 58. In the locked position of the slide locking mechanism 140, the bore 145 of the slide lock sleeve 141 engages the curved surface members 142 which are located in the frustum-conical holes 108 of the lower jaw member 58 causing the curved surface members 142 to partially protrude into the space 101 of the lower jaw member 58 and thus engage the groove 121 of the adjustable post 17. In the locked position, the spring 143 biases the shoulder 150 of the slide lock sleeve 141 against the snap ring 147.

To place the sliding lock mechanism in the unlocked position, the slide lock sleeve 141 is depressed in a downward direction, compressing the spring 143 against the snap ring 144. The slide lock sleeve 141 moves downward until the channel 146 of the slide lock sleeve 141 aligns with the frustum-conical holes 108 in the lower jaw member 58 permitting the curved surface members 142 to partially exit the frustum-conical holes 108 and thereby permitting the curved surface members 142 to withdraw from the groove 121 in the adjustable post 17. The withdrawal of the curved surface members 142 from the groove 121 in the adjustable post 17 frees the adjustable post 17 from its locked position and permits the longitudinal adjustment of the adjustable post 17 either up or down. Holding the slide lock sleeve 141 in the depressed position permits the adjustable post 17 to be adjusted without intermediate engagement of the curved surface members 142 into the grooves 121 of the adjustable post 17.

When the adjustable post 17 is longitudinally adjusted such that the groove 121 of the adjustable post 17 does not align with the bore 145 of the slide lock sleeve 141 and the adjustable post 17 is in the unlocked position, slide lock sleeve may be released returning it to its unbiased position. In this position, the bore 145 engages the curved surface members 142 and urges curved surface members 142 against the adjustable post 17. The curved surface members 142 may then engage the outer surface of the adjustable post 17. With slide lock sleeve 141 in this position, the adjustable post 17 may then be adjusted until the curved surface members 142 engage the next groove 121 in the adjustable post 17 and lock the adjustable post 17 at the desired position.

An alternative embodiment of the technology for rotating jaw drive member 62 is illustrated in FIGS. 9 through 11. FIG. 9 illustrates the same elements of FIG. 4 of the jaw drive member 62, however the four protruding areas 96, 97, 98, 99 shown in FIG. 4A on the top of the jaw drive member 62 and the pair of manual control handles 86, 87 disposed at the uppermost end of the jaw drive member 62 have been eliminated. Referring to FIG. 9, the upper portion of the jaw drive member 62 is formed with a plurality of ratchet teeth 260 on the periphery of the drive member 62.

FIG. 10 illustrates a side view of a reversible ratchet assembly 300. The reversible ratchet assembly 300 can engage the ratchet teeth 260 on the jaw drive member 62. With the reversible ratchet assembly 300 engaged on the ratchet teeth 260 of the jaw drive member 62, the reversible ratchet assembly 300 can rotate the jaw drive member 62 in a clockwise or a counter-clockwise direction. The clockwise rotation of the jaw drive member 62 drives the upper jaw member 60 downwardly, forcing the lower lip 106 of the lower jaw member 58 and the upper lip 81 of the upper jaw member 60 toward one another to engage the table rail 15. The jaw drive member 62 is rotated until the lower jaw lip 106 on the jaw drive member 62 and the upper jaw lip 81 of the upper jaw member 60 securely tighten against the rail 15.

With the reversible ratchet assembly 300 engaged on the ratchet teeth 260 on the jaw drive member 62 and set to ratchet in a counter-clockwise direction, the counter-clockwise rotation of the jaw drive member 62 causes the upper jaw member 60 to recede from the lower jaw member 58 untightening the lower jaw lip 106 on the jaw drive member 62 and the upper jaw lip 81 of the upper jaw member 60 from the rail 15.

The reversible ratchet assembly 300 includes a handle 220 operatively connected to a head 270. The head 270 defines a bore 290 for receiving the ratchet teeth 260 on the jaw drive member 62. FIG. 11 illustrates the engagement of the reversible ratchet assembly 300 with the ratchet teeth 260 on the jaw drive member 62. The head 270 includes a pawl 210, a compression spring 266, and a ball 264. The pawl 210 is rotatable about the axis of a pawl pin 230. The pawl 210, the compression spring 266, and the ball 264 are retained in the head 270 by a cover plate 275.

The pawl 210 has a first side 276 with a pair of engagement teeth 254, 250 and a second opposite side 277 with a pair of cam surfaces 261, 267. In FIG. 11, the engagement tooth 254 is engaged with the ratchet teeth 260. For clockwise rotation of the jaw drive member 62, the pawl 210 may rotate in its operating condition between an engaged position with the engagement tooth 254 engaged with the ratchet teeth 260 and a disengaged position. For counter-clockwise rotation of the jaw drive member 62, the pawl 210 may rotate in its operating condition between an engaged position with the teeth 250 engaged with the ratchet teeth 260 and a disengaged position.

During ratcheting movement of the reversible ratchet assembly 300, the pawl 210 oscillates between engaged and disengaged positions. Upon rotation from the engaged position of the engagement teeth 254 with the ratchet teeth 260 of the jaw drive member 62, the pawl 210 second opposite side 277 cam surface 267 interacts with a bias mechanism in which the ball 264 is biased against pawl 210 by the compression spring 266. As the engaged teeth of the ratchet teeth 260 cams past the engagement tooth 254, the spring 266 causes the ball 264 to ride on the second cam surface 267 to urge the pawl 210 back toward position for engagement with the next tooth of the ratchet teeth 260.

To rotate the jaw drive member in the counter-clockwise direction, the pawl 210 can be rotated so the engagement tooth 250 engages the ratchet teeth 260. Upon rotation from the engaged position of the engagement teeth 250 with the ratchet teeth 260 of the jaw drive member 62, the pawl 210 second opposite side 277 cam surface 261 interacts with a bias mechanism in which the ball 264 is biased against the pawl 210 by the compression spring 266. As the engaged teeth of the ratchet teeth 260 cams past the pawl tooth 250, the spring 266 causes the ball 264 to ride on the second cam surface 261 to urge the pawl 210 back toward position for engagement with the next tooth of the ratchet teeth 260.

The ratcheting of reversible ratchet assembly 300 can ratchet the jaw drive member in a 62 in a clockwise or counter-clockwise rotation depending on the position of pawl 210.

Referring to FIGS. 12-15, an alternative embodiment of a locking device to allow for height adjustment of adjustable post 17 is illustrated. In FIG. 12, an alternate embodiment for the lower jaw member 58 is illustrated. An end portion 125 of the lower jaw member 58 has a plurality of slots 130 in the sidewalls of the lower jaw member 58. The slots 130 in the lower jaw member 58 form a plurality of flexible fingers 135.

Figure 13:
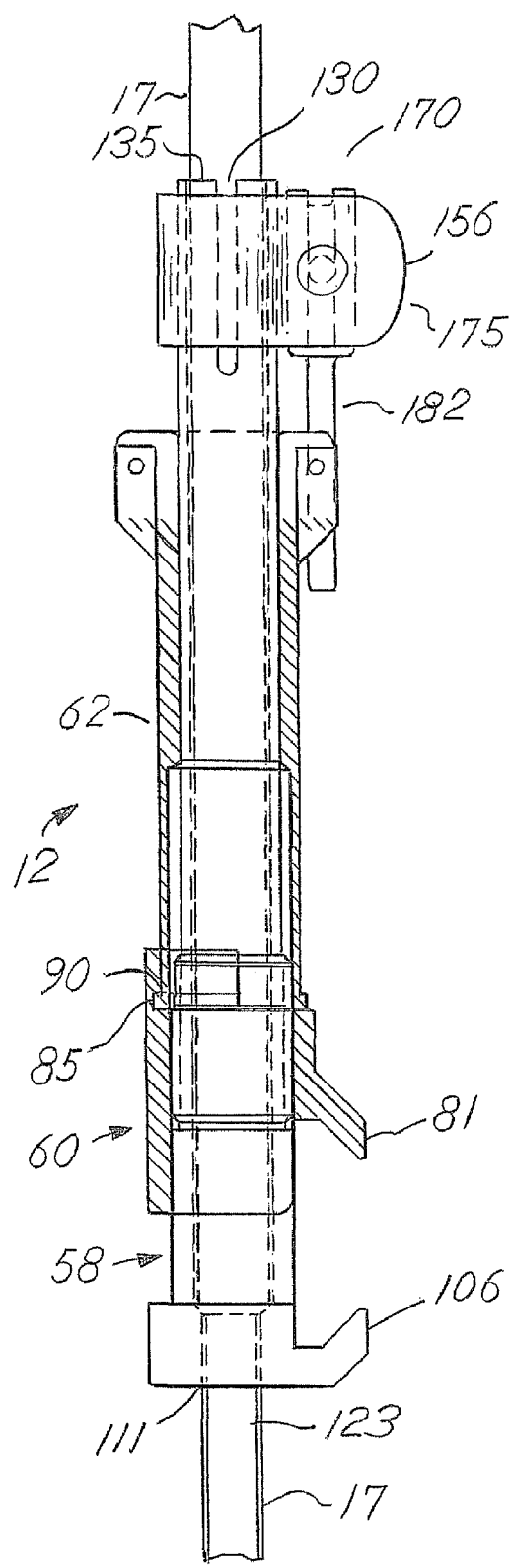
FIG. 13 is an elevated view of a rail clamp assembly with a cam tightened clamp locking device for quick height adjustment of support post.
Figure 14:
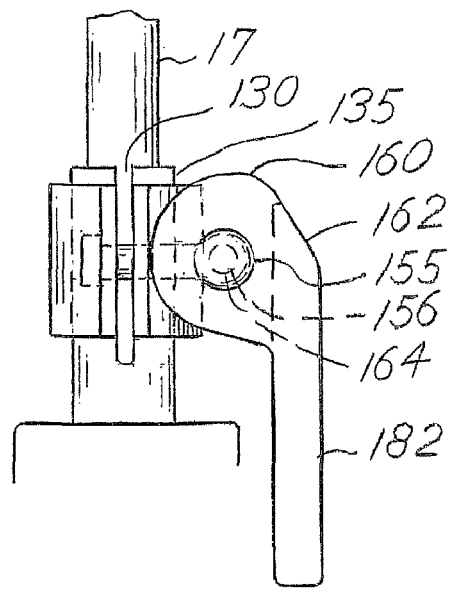
FIG. 14 is a side view of the cam tightened clamp locking device.
Figure 15:
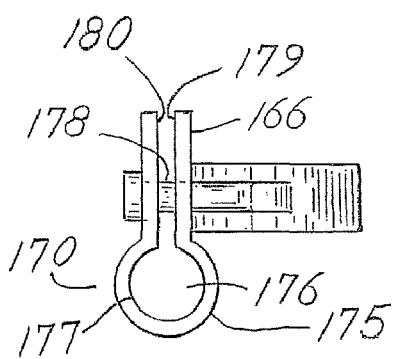
FIG. 15 is a top view of the cam tightened clamp locking device.

Referring to FIGS. 13-15, a locking device 170 using a cam tightened clamp can be used to lock the height of the adjustable post 17. The locking device includes a clamp 175. The clamp 175 includes a cylindrical passage 176 for receiving the slots 130 in the end portion 125 of the lower jaw member 58. The cylindrical passage 176 is defined by a broken cylindrical surface 177. The cylindrical surface 177 is broken along two parallel faces 178 and 179 which run the length of the clamp 175 to define a gap 180.

The clamp 175 includes a cam lever 182 as shown in FIGS. 13 and 14. The cam lever 182 is pivotally connected to a shaft 155 through a bore 164 by a pin 156. The shaft 155 operatively connects the cam lever 182 to the clamp 175. The cam lever 182 is pivotally moveable about the shaft 155 between an open position and a closed position. An outer edge 160 of a cam portion 162 of the cam lever 152 is eccentric such that the distance between the center of the bore 164 in the cam lever 152 and a top 166 of the clamp 175 increases as the cam lever is moved from its open position to its closed position. Movement of the cam lever 182 towards its closed position closes the gap 180 between the parallel faces 178 and 179. As the parallel faces 178, 179 of clamp 175 come closer together, the area circumscribed by the cylindrical passage 176 is constricted and the circumference of the flexible fingers 135 is reduced to grip the adjustable post 17 locking its movement.

Rotation of the cam lever 182 to its open position increases the cylindrical passage 176 allowing the flexible fingers 135 of the lower jaw member 58 to expand and release the grip on the adjustable post 17. With the cam lever 182 in the open position, adjustable post 17 is free to move allowing for adjustment.

While the invention has been described with reference to preferred embodiments, it will be understood by those skilled in the art that various changes may be made and equivalents substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed, but that the invention will include all embodiments falling within the scope of the appended claims.

The invention claimed is:

1. A surgical retractor system for attachment to a rail of a conventional surgical table comprising:
   a rail clamp assembly that includes a lower jaw member, the lower jaw member having an upper portion and a lower portion, the upper portion of the lower jaw member having a plurality of radially spaced frustum conical sockets, the lower jaw member having an outer surface and an inner surface, the lower jaw member having a bored upper portion to form a cylindrical inside surface and a lower portion with a hollowed non-cylindrical uniform aperture having a first end in communication with the cylindrical bored upper portion and a second end open to atmosphere, the lower jaw member having a first jaw surface adapted for seating against one portion of the rail, the lower jaw member having a first set of threads disposed along a portion of the outer surface of the lower jaw;
   an upper jaw member having an outer surface and an inner surface, the inner surface of the upper jaw member disposed over the outer surface of the lower jaw member, the upper jaw member having a second jaw member for seating against one portion of the rail, the upper jaw member having a semi-circular section having a guide slot;
   a jaw drive member having an outer surface and an inner surface, the inner surface disposed on the outer surface of the lower jaw member, the jaw drive member having a second set of threads disposed on one section of the inner surface of the jaw drive member, the first set of threads of the lower jaw member mateable with the second set of threads of the jaw drive member for causing movement of the upper jaw member relative to the lower jaw member;
   a post extending slidably upward through the rail clamp assembly, the post having a cylindrical upper portion and a non-cylindrical lower portion, the upper portion having a plurality of circumferential grooves;
   a locking device for releasably locking the post relative to the upper portion of the lower jaw member in a plurality of longitudinally spaced positions; and
   a turning member for manually causing relative movement of the jaw drive member.

2. A surgical retractor system according to claim 1, wherein the locking device comprises an outer sleeve slidably positioned on the upper portion of the lower jaw member, a plurality of curved surface members housed between the sleeve and the upper portion of lower jaw member for engaging the plurality of frustum conical sockets of the upper portion of the lower jaw member, a spring biasing the outer sleeve between a first position and a second position, and a plurality sleeve positioning restraints for engagement of an upper and a lower accurate slots in the upper portion of the lower jaw member.

3. A surgical retractor system according to claim 2, wherein the sleeve position restraints are snap washers for engagement in the upper and the lower accurate slots in the upper portion of the lower jaw member.

4. A surgical retractor system according to claim 2, wherein a smaller diameter of the frustum conical sockets in the upper portion of the lower jaw member is on the inner surface of the lower jaw member with the smaller diameter less than a diameter of the curved surface members to allow the curved surface members to partially protrude past the inner surface of the lower jaw member.

5. A surgical retractor system according to claim 2, wherein the outer sleeve includes an upper inner shoulder, a lower inner shoulder and a channel for accepting the curved surface members.

6. A surgical retractor system according to claim 5, wherein the outer sleeve in the first position causes the lower inner shoulder to engage the curved surface members disposing the curved surface members into the frustum conical sockets of the lower jaw member, the curved surface members protruding past the inner surface of the lower jaw member engaging the circumferential grooves of the post member positively locking the post member against relative longitudinal movement.

7. A surgical retractor system according to claim 5, wherein the outer sleeve in the second position aligns the channel in the sleeve with the holes permitting movement of the curved surface members out of the frustum conical sockets into the channel in the sleeve thus unlocking the post member allowing relative longitudinal movement of the post relative to the outer sleeve.

8. A surgical refractor system according to claim 1, wherein the non-cylindrical lower portion of the lower jaw member is sized to receive insertion of the non-cylindrical portion of the post member, wherein the non-cylindrical portion of the post member extends through the hollowed non-cylindrical hole to prevent the rotation of the post within the lower jaw member.

* * * * *